(12) United States Patent
Knebel-Doeberitz et al.

(10) Patent No.: US 6,743,423 B1
(45) Date of Patent: Jun. 1, 2004

(54) USE OF ADENO-ASSOCIATED VIRUSES FOR DECREASING THE RADIOTHERAPY-INDUCED OR CHEMOTHERAPY- INDUCED RESISTANCE IN CANCER PATIENTS

(75) Inventors: Mangus Von Knebel-Doeberitz, Heidelberg (DE); Petra Klein-Bauernschmitt, Heidelberg (DE); Harald Zur Hausen, Waldmichelbach (DE); Jörg Schlehofer, Leimen (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 09/719,336

(22) PCT Filed: Jun. 8, 1999

(86) PCT No.: PCT/DE99/01711

§ 371 (c)(1),
(2), (4) Date: Mar. 22, 2001

(87) PCT Pub. No.: WO99/64024

PCT Pub. Date: Dec. 16, 1999

(30) Foreign Application Priority Data

Jun. 8, 1998 (DE) ......................................... 198 25 620

(51) Int. Cl.⁷ .......................... A61K 48/00; C12N 7/00; A01N 63/00
(52) U.S. Cl. ..................... 424/93.6; 435/235.1; 514/44; 424/93.1
(58) Field of Search ............................... 424/93.1, 93.6; 514/44; 435/235.1

(56) References Cited

FOREIGN PATENT DOCUMENTS

| DE | WO96/18737 | 6/1996 |
|----|------------|--------|
| DE | 4444949    | 11/1996 |

OTHER PUBLICATIONS

Verma et al., Gene Therapy Promises, problems and Prospects, Nature, vol. 389, p. 239, col. 1.*
Gura, Systems for identifying new drugs are often faulty, 1997, Science, vol. 278, pp. 1041–1042.*
Klein–bauernschmitt et al., Improved efficacy of chemotherapy by parvovirus–mediated sensitisation of human tumour cells, 1996, European Journal of Cancer, vol. 32A, pp. 1774–1780.*
Walz et al., Adeno–associated viruses sensitizes HeLa cell tumors to gamma rays, 1992, Journal of Virology, vol. 66, pp. 5651–5657.*
Russell et al., DNA synthesis and topoisomerase inhibitors increase transduction by adeno–associated virus vectors, 1995, Proc. Natl. Acad. Sci., vol. 92, pp. 5719–5723.*
M. von Knebel Doeberitz, et al.; Der Einfluβ molekularer Diagnostikverfahren auf die chirurgische Therapie maligner Erkrankungen; Chirurg (1996) 67; 967–979.
Song W, Kong HL, Traktman P, Crystal RG; Cytotoxic T lymphocyte responses to proteins encoded by heterologous transgenes transferred in vivo by adenoviral vectors.; Hum Gene Ther 1997 Jul. 1; 8(10):1207–1217.
Lois L. Myeroff, et al.; A Transforming Growth Factor β Receptor Type II Gene Mutation Common in Colon and Gastric but Rare in Endometrial Cancers with Microsatellite Instability; Cancer Research 55:5545–5547; Dec. 1, 1995.
Jing Wang, et al.; Demonstration That Mutation of the Type II Transforming Growth Factor β Receptor Inactivates Its Tumor Suppressor Acitivity in Replication Error–positive Colon Carcinoma Cells; The Journal of Biological Chemistry (Sep. 1995) Vo. 270. No. 37:pp. 22044–22049.
Jean Marx; DNA Repair Defect Tied to Mutated TGF–β Receptor Gene; Science, vol. 268 (Jun. 2, 1995), pp. 1276–1277.
Rhonda F. Souze, et al.; Microsatellite instability in the insulin–like growth factor II receptor gene in gastrointestinal tumors; Nature Genetics, (Nov.1996) vol. 14, pp. 255–257.
Wenru Song, et al.; Cytotoxic T Lymphocyte Responses to Proteins Encoded by Heterologous–Transgenes Transferred *in vivo* by Adenoviral Vectors; Human Gene Therapy (Jul. 1, 1997) 8:1207–1217.
David O. Morgan, et al.; Insulin–like growth factor II receptor as a multifunctional binding protein; Nature (Sep. 24, 1987) Vo. 329:pp 301–307.
Chemical Abstracts: vol. 125; Dec. 2, 1996; No. 23; pp. 50.
Chemical Abstracts: vol. 117; Oct. 26, 1992; No. 17; pp. 389.
Chemical Abstracts: vol. 113; Sep. 10, 1990; No. 11; pp. 34.
P. Klein–Bauernschmitt, et al.; Improved Efficacy of Chemotherapy by Parvovirus–mediated Sensitisation of Human Tumour Cells; European Journal of Cancer (1996); vol. 32A, No. 10 pp. 1774–1780.
M. Hillgenberg, et al.; Enhanced Sensitivity of Small Cell Lung Cancer Cell Lines to Cisplatin and Etoposide After Infection with Adeno–associated Virus Type 2; European Journal of Cancer (1999); vol. 35, No. 1; pp. 106–110.

* cited by examiner

*Primary Examiner*—Anne-Marie Falk
*Assistant Examiner*—Celine Qian
(74) *Attorney, Agent, or Firm*—Marianne Fuierer; Steven J. Hultquist; Yongzhi Yang

(57) ABSTRACT

The invention relates to the use of adeno-associated viruses for decreasing the radiotherapy-induced or chemotherapy-induced resistance in patients who suffer from a cancer which is to be treated by radiotherapy or chemotherapy.

9 Claims, 4 Drawing Sheets

USE OF ADENO-ASSOCIATED VIRUSES FOR DECREASING THE RADIOTHERAPY-INDUCED OR CHEMOTHERAPY- INDUCED RESISTANCE IN CANCER PATIENTS

CROSS-REFERENCE TO RELATED APPLICATIONS

This application is filed under the provisions of 35 USC §317 and claims the priority of International Patent Application No. PCT/DE99/01711 filed Jun. 8, 1999, which in turn claims priority of German Patent Application No. 198 25 620.5 filed Jun. 8, 1998.

BACKGROUND OF THE INVENTION

1. Field of Invention

The invention relates to the use of adeno-associated viruses for decreasing the radiotherapy-induced or chemotherapy-induced resistance in patients who suffer from a cancer which is to be treated by radiotherapy or chemotherapy.

2. Description of Related Art

Along with the removal by surgery malignant diseases have been treated by radiotherapy and/or chemotherapy thus far. However, the occurrence of side-effects, in particular the development of resistances, limits the use of cytostatic agents. Because of these side-effects chemotherapeutic agents can only be used to a limited extent. Thus, the dosage of a chemotherapeutic agent can only be a dosage which the patient tolerates. However, in most cases such a dosage only achieves a minor curative effect.

SUMMARY OF THE INVENTION

Therefore, it is the object of the present invention to reduce or attenuate the problem of resistance induced by radiotherapy or chemotherapy so as to improve the survival rate of cancer patients after a radiotherapy or chemotherapy. In addition, it shall be possible to reduce the subsequent doses of a radiotherapy or chemotherapy. The responsiveness of tumor cells to radiotherapy or chemotherapy shall also be improved.

This object is achieved by the subject matters defined in the claims.

According to the invention the development of a radiotherapy-induced or chemotherapy-induced resistance in patients suffering from a cancer to be treated by radiotherapy or chemotherapy shall be reduced by using adeno-associated viruses.

It was found surprisingly that following a treatment with humans non-pathogenic adeno-associated viruses (AAV) the tumor cells respond in a better way to a subsequent chemotherapeutic or radiotherapeutic measure.

The AAV virus is a human parvovirus which requires co-infection with a helper virus for a productive infection to take place. AAV infects human in their infancy and is considered non-pathogenic, since no human disease could be correlated with the AAV infection (Adv. in Vir. Res., 1987, 32, 43–306).

According to the inventors' insight, an AAV infection in combination with chemotherapeutic or radiotherapeutic measures increases the efficiency of a conventional therapy and reduces resistances which occur, so that a further therapy can be carried out in a more promising way than possible thus far. Any AAV viruses can be used according to the invention. The AAV-2 virus is used preferably.

In animal experiments carried out with immunodeficient nude mice into which small cell lung carcinoma cells were implanted subcutaneous, it could be shown that an AAV infection which was carried out at the same time as a chemotherapy resulted in a faster recession of the tumors. Relapses occurred after a short time in both group. However, in the AAV-infected chemotherapeutic group they responded better to another chemotherapy than those of the group only treated by means of chemotherapy. This shows that an AAV infection can reduce or even avoid the development of resistances.

The use of the AAV viruses according to the invention can be made before, at the same time with or after the chemotherapy or radiotherapy. However, it is carried out preferably after a first chemotherapeutic or radiotherapeutic treatment cycle.

In particular in the case of tumor kinds which per se show a poor response to a chemotherapy or radiotherapy it may be indicated to carry out the treatment before or together with the chemotherapy/radiotherapy to increase the efficiency of the therapy. By this the treatment doses can be lowered and therefore the side-effects can be reduced.

The radiotherapy or chemotherapy may be any radiotherapy or chemotherapy which is adapted to the cancer to be treated. Such therapies have been known for years and along with the removal of the tumor by surgery that represent the established method of curing cancer diseases or increasing the life expectancy of a patient by some time. Therefore, a person skilled in the art is perfectly familiar with the measures of a radiotherapy or chemotherapy.

The use of AAV viruses according to the invention can be applied to any cancer kinds, the best success being expectable in connection with colon cancers, pancreatic carcinomas and brain tumors (in particular glioblastomas). The small cell lung carcinoma (SCLC) can preferably be treated therewith.

The application according to the invention is made intravenously, by means of infusions, intratumorally, orally (also by means of inhalations) or cutaneously. In this connection, the virus is formulated in a suitable preparation adapted to the pathway of administration. For an intravenous (also as an infusion) and intratumoral administration it is preferred to provide the virus in a physiological common salt solution, Ringer's solution or PBS solution (phosphate-buffered salt solution), for a cutaneous administration it is preferred to provide it in the form of an ointment, suspension or gel, and for oral administration it is preferred to provide it in the form of an aerosol spray.

Depending on the patient's body weight the virus dose employed is $10^9$–$10^{10}$ AAV particles/kg body weight.

A pharmaceutical composition is also provided according to the invention which in addition to the chemotherapeutic agent (cytostatic agent) contains adeno-associated viruses, in particular AAV-2. All chemotherapeutic agents (cytostatic agents) common in tumor therapy thus far can be used separately or in combination as a chemotherapeutic agent, e.g. cisplatin, etoposide, methothrexate, doxorubicin, cyclophosphamide trofosfamide, busulfane, cytarabin, fluorouracil, mercaptopurins, vinblastinesulfate, vincristinesulfate, bleomycinsulfate or mitomycin. Thus, it is preferred for an intravenous (also by mean of infusion) and intratumoral administration to provide an injection solution, for a cutaneous administration to provide an ointment, for an oral administration to provide an aerosol spray. As a basis for the preparation of the infusion solution physiological common salt solution, Ringer's solution or PBS each are suitable in pure form or as a mixture. The amount of AAV depends on the patient's weight and is $10^9$–$10^{10}$ particles/kg body weight. In the pharmaceutical composition it is contained in an amount suitable for an average body weight of 70 kg. The accurate dosage of the pharmaceutical composition according to the invention is determined by a physician and depends on the patient's sex and weight, severity of the disease, kind of administration and planned duration of administration. A composition according to the invention may also contain conventional auxiliary agents. The common auxiliary agents such as carriers, binders, blasting agents, lubricants, solvents, solubilizers, release accelerators, release decelerators, emulsifiers, stabilizers, colorants of the taste correctives may be used as auxiliary agents.

The invention is explained in more detail by means of the attached figures.

DETAILED DESCRIPTION OF THE INVENTION

Figure 1:
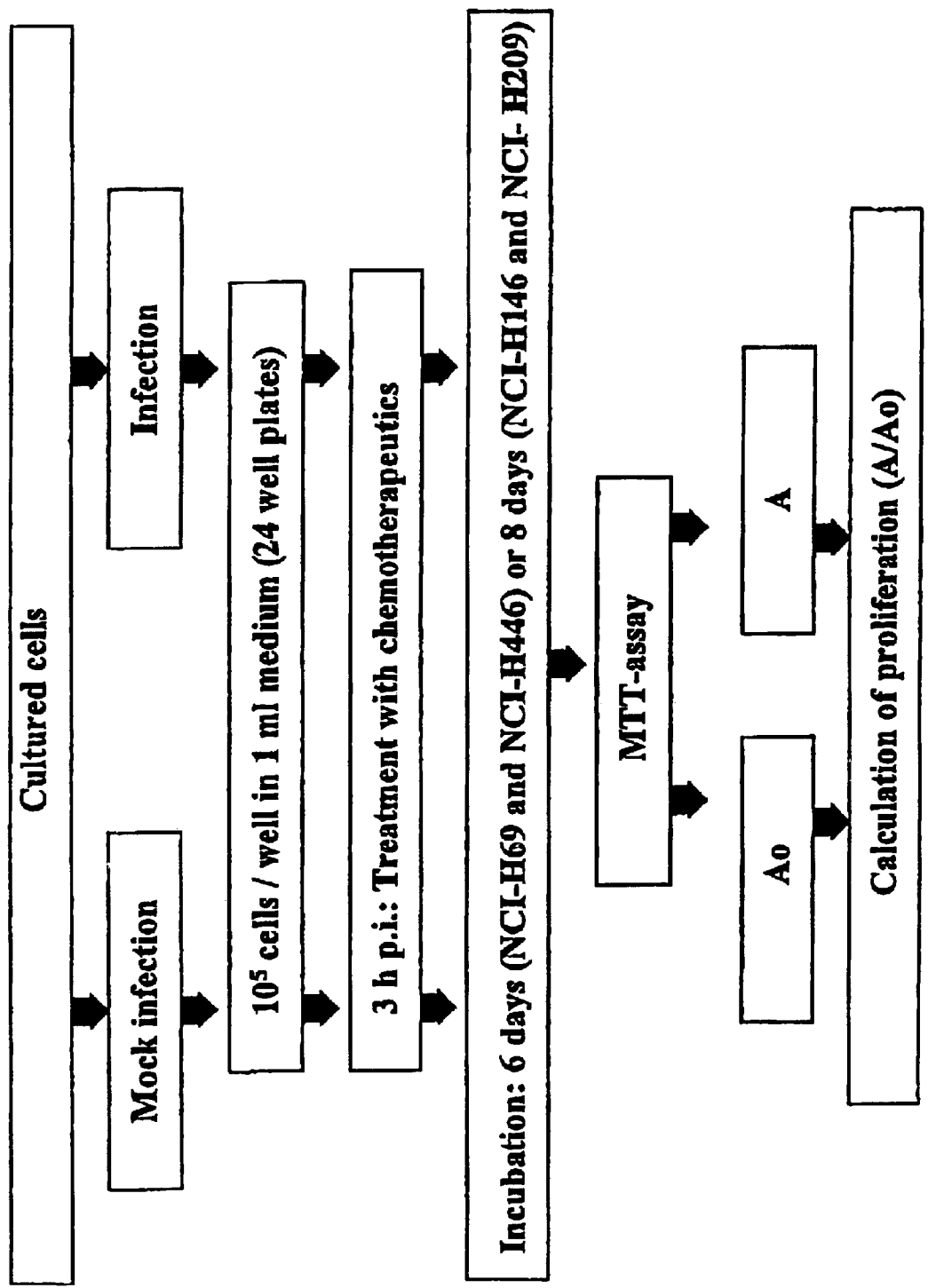
FIG. 1 shows a diagram of the protocol used for determining AAV-2 mediated drug-sensitization. The proliferation of the SCLC cell lines after the infection and/or drug treatment was determined by the MTT assay (J Immunol. Methods, 1983, 56, pp. 55–63). The relative proliferation (A/Ao) was calculated by the ratio absorption of AAV-2-infected and/or drug-treated cells (A) to absorption of mock-infected untreated cells (Ao).

The invention is explained in more detail by way of the small cell lung carcinoma (SCLC). This carcinoma type is generally characterized by an initially effective chemotherapy and remission of the tumor. However, almost all of the patients suffer from a relapse which resulted from a resistance of the tumor cells to the first applied chemotherapy (usually cisplatin/etoposide). Therefore, it was tested in a model system with a human small cell lung carcinoma cell line whether an infection with AAV enhances the cytotoxic effect of the chemotherapeutic agents in the cell culture and in tumors of immunodisturbed mice. It is shown that the AAV infection increases significantly the effectiveness of the chemotherapy of SCLC tumor cells and SCLC tumors.

EXAMPLE 1

Sensitization of SCLC Cell Lines Over Cisplatin and Etoposide by AAV Infection Small cell lung carcinoma cell lines (NCI-H69, NCI-H164, NCI-H209, and NCI-H446) (Cancer Res., 1980, 40, 3502–3507; Cancer Res., 1985, 45, 2913–2923) were cultured in RPMI-1640 medium (Eurobio, Raunheim, Germany). HeLa cells were cultured in DMEN (Eurobio, Raunheim, Germany). All growth media were supplemented with glutamine (Eurobio, 1%), antibiotics (penicillin and streptomycin) and 10% heat-inactivated fetal calf serum (PAA; Liz, Austria). The cultures were incubated at 37° C. in a damp atmosphere with 5% $CO_2$ and tested for mycoplasma contaminations at regular intervals.

The adeno-associated virus type 2 (AAV-2) was replicated in HeLa cells using, adenovirus type 2 (Ad-2) as a helper. AAV was purified in a cesium-chloride gradient and titrated as described in J. Gen. Virol., 1994, 74, 2655–2662. The adenovirus type 2 inocula were clarified supernatants of Ad-2-infected HeLa cells.

The SCLC cells were suspended in PBS and incubated with purified AAV-2 in the indicated multiplicities of infection (MOI). After 45 min at 37° C., unbound absorbed virus was removed by washing using PBS and the growth medium was supplemented. Either PBS or the heat-inactivated fraction (56° C., 30 min) of a CsCl gradient of Ad-2-infected cells alone was used for the controls (mock infection), the density (1.14 g/$cm^3$) of the AAV-2-containing fraction which was used for the AAV-2 purification being indicated in the respective experiments. The volume/cell ratio of these experiments was 50 times greater (5 ml/$16^8$ cells) than the one used for the AAV infections.

The AAV-2-infected or mock-infected cells were treated with cisplatin. (Astra Medica, Frankfurt/Main, Germany) or etoposide (Bristol, Munich, Germany) or both in a ratio [cisplatin:etoposide=1:2:5], the pharmacons dissolved in PBS, being added to the medium in the indicated concentration.

The proliferation of the SLCL cells after the infection with AAV-2 and/or treatment with chemotherapeutic agents was determined by the modified MTT test (J. Immunol. Methods, 1983, 56, 55–63). After the infection or mock infection, the cells were placed in plates having 24 wells with a density of $10^5$ cells/well and treated with the chemotherapeutic agents in the indicated concentrations. After six days, (NCI-H69, NCI-H-446) or eight days (NCI-H46, NCI-H209), MTT, (3'-(4,5-dimethylthiazole-2-yl)-2,5-diphenyltetrazoliumbromide; Sigma, Deisenhofen, Germany) was added to the culture up to a final concentration of 0.5 mg/ml. The cultures were then incubated at 37° C. for 4 h to permit a reduction of MTT into blue formazan by mitochondrial dehydrogenases (Arch Biochem. Biophys., 1993, 303, 474–462), which indicates active proliferation of the cells. The cells were centrifuged, washed with PBS, and formazan was solubilized in isopropanol. The precipitated proteins were pelleted by centrifugation (1000 rpm, 15 min), and 200 ul samples of the supernatant were measured to determine the optical density at 540 nm (OD540), OD690 being used as a reference and a Titertek Multiskan plus MKII densitometer being employed (Lab Systems, Finland).

The relative proliferation (A/Ao) was defined as the ratio of the absorption (A) measured in the supernatant of AAV-2-infected and/or pharmacon-treated cells, compared with the absorption measured for the supernatant of the mock-infected cells and untreated control cells (Ao). The $IC_{50}$ value was defined as pharmacon concentrations resulting in a 50% inhibition of proliferation.

The AAV-2-infected cells (MOI values as indicated) or mock-infected cells were placed in plates having 24 wells and treated with cisplatin. After six or eight days, the relative proliferation was determined. In addition, kinetic studies were carried out to determine the optimum treatment modalities for SCLC cells after an AAV infection. It was shown in these investigation that the AAV-mediated sensitization reached a maximum after one to three hours following the infection. In this investigation the chemotherapeutic agents were administered three hours after the AAV infection. In order to exclude effects which are due to factors still present after the purification with the CsCl gradient and the Ad-2 heat inactivation, a control, of the mock infection with PBS was carried out in addition to the mock infection with the fraction of the respective gradient of a cell lysate of Ad-2-infected cells.

The relative proliferation of NCI-H209-SCLC cells and NCI-H446-SCLC cells was measured after the infection with various multiples of the infectious units (MOI) of AAV-2 ($10^2$–$10^5$, tissue culture infectious dose (TCID per cell) with and without subsequent treatment with cisplatin with the $IC_{50}$ values listed in Table 1.

TABLE 1

Concentration of the chemotherapeutic agents which result in a 50% inhibition of the proliferation ($IC_{50}$) of the SCLC cell lines

| Cells Type | Cisplatin | Etoposide | Cisplatin/etoposide |
|---|---|---|---|
| NCI-H69 | 0.2 | 0.26 | 0.08/0.2 |
| NCI-H146 | 0.11 | 0.025 | 0.008/0.02 |
| NCI-H209 | 0.007 | 0.053 | 0.006/0.015 |
| NCI-H446 | 0.15 | 0.21 | 0.042/0.105 |

As shown in Table 1, the SCLC cell lines NCI-H69 and NCI-H446 showed a high intrinsic resistance towards both pharmaceutical preparations. The susceptibility to cisplatin/etoposide treatment being lesser, whereas: NCI-H146 cells were highly susceptible to etoposide and the NCI-H209 cells were highly susceptible to both pharmacons.

Figure 2A:
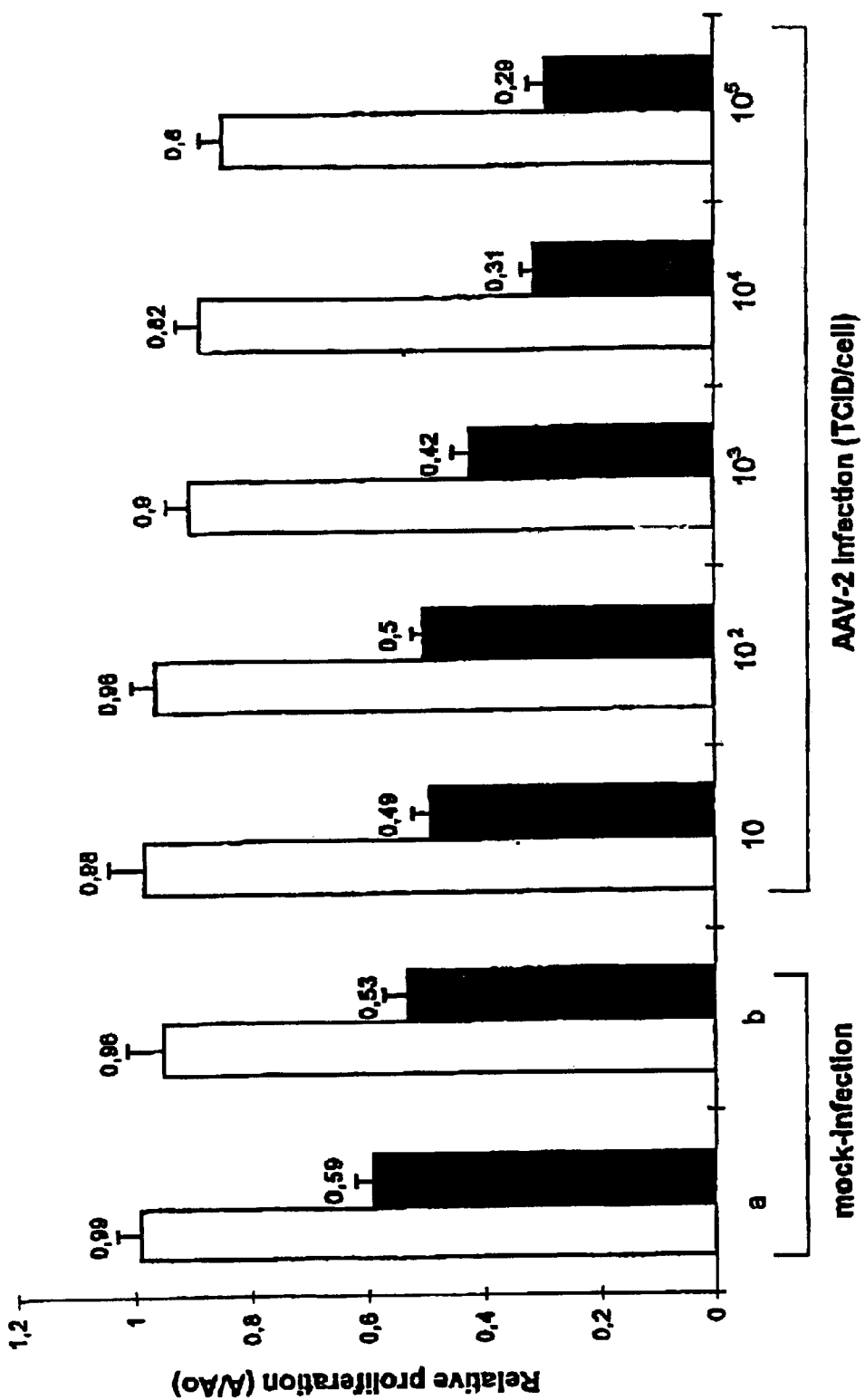
FIGS. 2a and [+] b show the AAV-mediated sensitization of the SCLC cell lines over cisplatin, the relative proliferation (A/Ao) of the SCLC cell lines, NCI-H209 (FIG. 2a) and NCI-H446 (FIG. 2b) following a mock infection (a: PBS alone; b: infected with a heat-inactivated gradient of Ad-2-infected cells) or infection with various multiplicities of an infection (MOI) with AAV-2 with (black columns) or without (white columns) subsequent treatment with $IC_{50}$ of cisplatin according to Table 1 (TCID, tissue culture infectious dose)
Figure 2B:
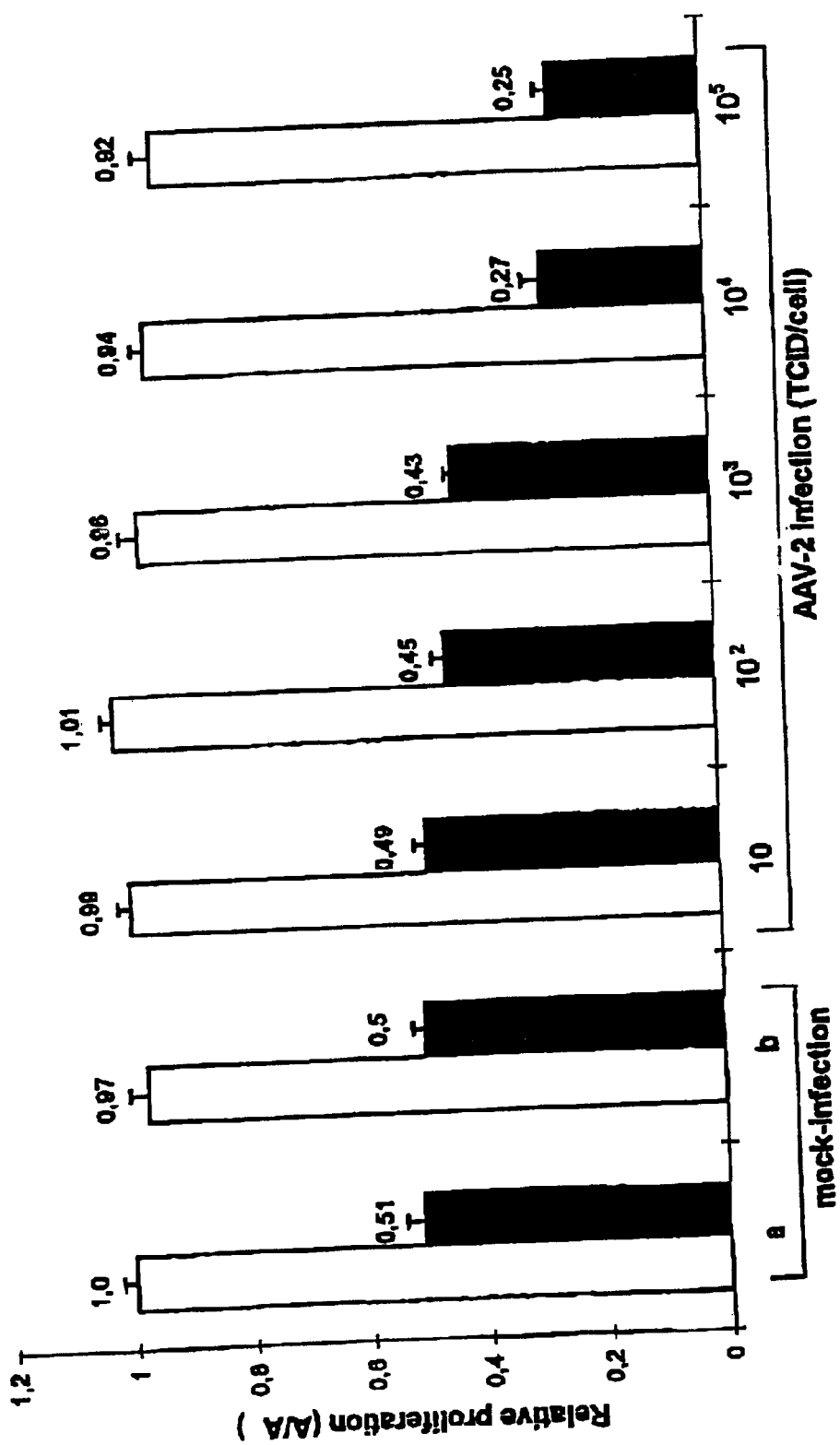

As follows from FIG. 2 (a+b), the AAV-2 infection resulted in a decrease of the proliferation rate of the cisplatin-treated cells with a MOI of $10^3$–$10^4$ TCID/cell. The infection with a MOI of $10^5$ TCID/cell resulted in no further increase. No significant inhibition of the proliferation was observed after the infection with lower MOI values of AAV-2 or after the mock infection, which indicates a specific effect due to the infection with high MOI or AAV-2. The relative proliferation of AAV-2-infected ($10^{3-5}$ (AAV/cell) and with cisplatin-treated (IC50) cells was lowered to 0.29 in NCI-H446 cells and to 0.25 in NCI-H209 cells as compared to the relative proliferation (IC50) cells treated only with cisplatin (0.59 ln NCI-H446 cells and 0.5 in NCI-H209 cells)

EXAMPLE 2

Quantification of the AAV-2-Mediated Pharmacon Sensitization of SCLC Cell Lines

In order to quantify the sensitization of cells over chemotherapeutic agents after infection with AAV-2, dose-response curves were prepared. The relative proliferation of the cell lines was determined after a mock infection (PBS) or AAV infection with $10^3$ or $10^4$ TCID/cell and subsequent treatment with various concentrations of cisplatin or etoposide or a combination of both pharmaceutical preparations (Table 2).

TABLE 2

Sensitization factor of SCLC cell lines which were treated with cisplatin and/or etoposide and were infected with AAV.

| Cell line | Chemotherapeutic agent | Sensitization factor (A/Ao)* $10^4$ Ip.AAV/Cell |
|---|---|---|
| NCI-H69 | Cisplatin | 1.43 |
| | Etoposide | 1.30 |
| | Cisplatin/etoposide | 1.45 |
| NCI-H146 | Cisplatin | 1.37 |
| | Etoposide | 1.38 |
| | Cisplatin/etoposide | 1.33 |
| NCI-H209 | Cisplatin | 2.33 |
| | Etoposide | 2.12 |
| | cisplatin/etoposide | 2.00 |
| NCI-H446 | Cisplatin | 2.50 |
| | Etoposide | 3.00 |
| | Cisplatin/etoposide | 3.00 |

*The relative proliferation (A/Ao) was calculated by the ratio absorption of AAV-2-infected and/or pharmacon treated (A) cells to absorption of the mock-infected, untreated controls (Ao)

The sensitization factors (SF) were defined as the ratio of the $IC_{50}$ values of infected cells compared with the $IC_{50}$ values of mock-infected cells. The sensitization factor indicates the factor by which the concentration of a chemotherapeutic agent can be reduced after an infection with AAV-2 to obtain the same degrees of proliferation inhibition. As summarized in Table 2 the sensitization by AAV-2 in NCI-H669 and NCI-H146 was moderate (maximum SF about 1.4 with a MOI of $10^4$ TCID/cells). The infection of NCI-H209 or NCI-H446 induced a more significant MOI-dependent sensitization (maximum SF about 3 (NCI-H446) and 2.3 (NCI-H209) with a MOI of $10^4$ TCID/cell). The AAV-2-mediated sensitization did not depend on the chemotherapeutic agent employed.

EXAMPLE 3

AAV-2-Mediated Pharmacon Sensitization of NCI-H209-Derived Tumors in Nude Mice

H209 is a cell line which is derived from a tumor which was not treated chemotherapeutically before cultured and is not resistant to drugs.

Figure 3:
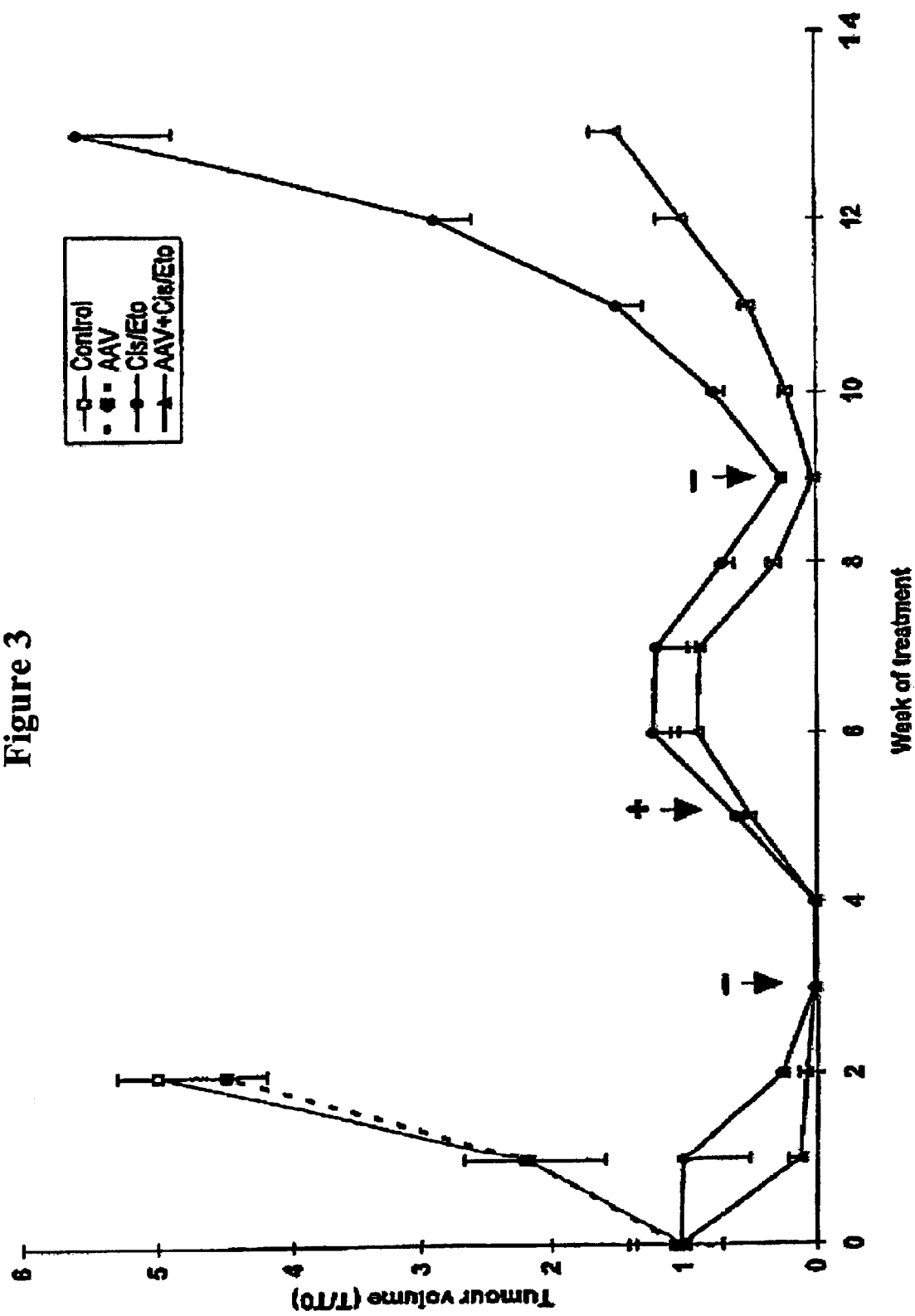
FIG. 3 shows the AAV-mediated sensitization of tumors in nude mice, derived from NCI-H209 cells (5 mice per group). The dose of cisplatin was 3 mg/kg body weight(weekly administration). The etoposide dose was 7.5 mg/kg body weight (administered three times a week). AAV-2 was administered weekly in a MOI of $10^8$ TCID/animal. Arrows show the change of the treatment modalities: – interruption of the drug treatment and AAV-2 infection; + beginning of the treatment and the infection.

Female nude mice (CD1-nu/nu) from Iffa Credo (Brussels, Belgium) were kept in isolators and were given water and food as desired. Experimentally growing SCLC cells (H209) were injected subcutaneously into the side of the six-week-old mice ($10^7$ cells in 100 ul PBS per animal). Five months after the inoculation of the cells, when the tumors had reached an average volume of 200 mm$^3$, the animals were infected weekly with AAV-2 (intratumoral injection of $10^8$ tissue culture infectious doses (TCID)) and/or with chemotherapeutic agents by intraperitoneal injection of 3 mg/kg body weight cisplatin (weekly) and 7.5 mg/kg body weight etoposide (three times a week). Details of the beginning and end of the treatment are indicated in FIG. 3. In each group (control, chemotherapeutic treatment, AAV2 infection, treatment+infection) five animals were received. The infected and non-infected animal were kept in separate isolators. The tumor diameters were measured weekly and the tumor volume was determined by the formula tumor volume=½×width×depth×height. The relative tumor volume (V/Vo) was determined for each animal and each time (ratio of the tumor volume [V] compared with the tumor at the beginning of the treatment ([Vo]).

As follows from FIG. 3, the treatment with chemotherapeutic agents resulted in a rapid decrease of the tumor volumes and a complete regression after three weeks of treatment. The combination of chemotherapy with AAV2 infection resulted in a more rapid decrease of the tumor volume compared with animals which had only received a chemotherapy, which indicates a sensitization of the pharmacon-treated tumor cells by AAV-2. The infection with AAV-2 alone had no significant effect, and the tumor volumes increased to the same extent as did the untreated controls. The treatment was discontinued after complete regression of the tumors and was resumed in the case of a relapse. The treatment of relapse was less effective with animals, which had only received drug treatment, as compared to the animals infected with AAV and treated chemotherapeutically. This shows the development of a resistance to the initial treatment at least in the chemotherapeutically treated animal group. The relapses in AAV-2-treated animals were still susceptible to cisplatin and etoposide treatment but the tumor regression was slower as compared to the regression of the initial tumors. In 3 of 5 AAV-2-infected animals the tumors regressed completely in week 9, in contrast to the tumors of animals which were only treated with chemotherapeutic agents, a complete regression of the tumor not being induced.

What is claimed is:

1. A method for lowering chemotherapy resistance in a patient being treated with a chemotherapeutic agent for a small cell lung or pancreatic cancer, the method comprising:

administering to the patient an effective amount of AAV-2 to lower the chemotherapy resistance to the chemotherapeutic agent, in combination with administering a chemotherapeutic agent, wherein the effective amount of AAV-2 is administered intratumorally; and determining if the chemotherapy resistance to the chemotherapeutic agent is lowered.

2. The method according to claim 1, wherein the AAV-2 is used in a dose of $10^9$–$10^{10}$ AAV particles/kg body weight.

3. The method according to claim 1 wherein the chemotherapeutic agent is selected from the group consisting of cisplatin, etoposide and cisplatin/etoposide.

4. The method according to claim 1, wherein the AAV-2 is administered before, after or simultaneously with a chemotherapy treatment.

5. A pharmaceutical composition containing a chemotherapeutic agent and an effective dose of AAV-2 to lower resistance of tumor cells to the chemotherapeutic agent in patients suffering from a cancer selected from the group consisting of pancreatic carcinoma, and small cell lung carcinoma, wherein the pharmaceutical composition is administered intratumorally.

6. The pharmaceutical composition according to claim 5, wherein the chemotherapeutic agent is selected from the group consisting of cisplatin, etoposide and cisplatin/etoposide.

7. The pharmaceutical composition according to claim 5 or 6, wherein the composition is formulated in an injection solution.

8. A method for enhancing chemosensitivity of cancer tumor cells to a chemotherapeutic agent to reduce tumor growth, the method comprising:

administering a sufficient amount of AAV-2 intratumorally to enhance chemosensitivity of the cancer tumor cells to the chemotherapeutic agent, in combination with administering the chemotherapeutic agent to the cancer cells, and determining if tumor growth is reduced, whereby a reduction in tumor growth indicates the chemosensitivity of cancer tumor cells is enhanced and wherein the tumor cells are selected from small cell lung cancer or pancreatic cancer.

9. The method according to claim 8, wherein the chemotherapeutic agent comprises an agent selected from the group consisting of: cisplatin, etoposide and cisplatin/etoposide.

* * * * *